July 2, 1946. W. E. LAMMERTS Plant Pat. 704
ROSE PLANT
Filed Feb. 8, 1945
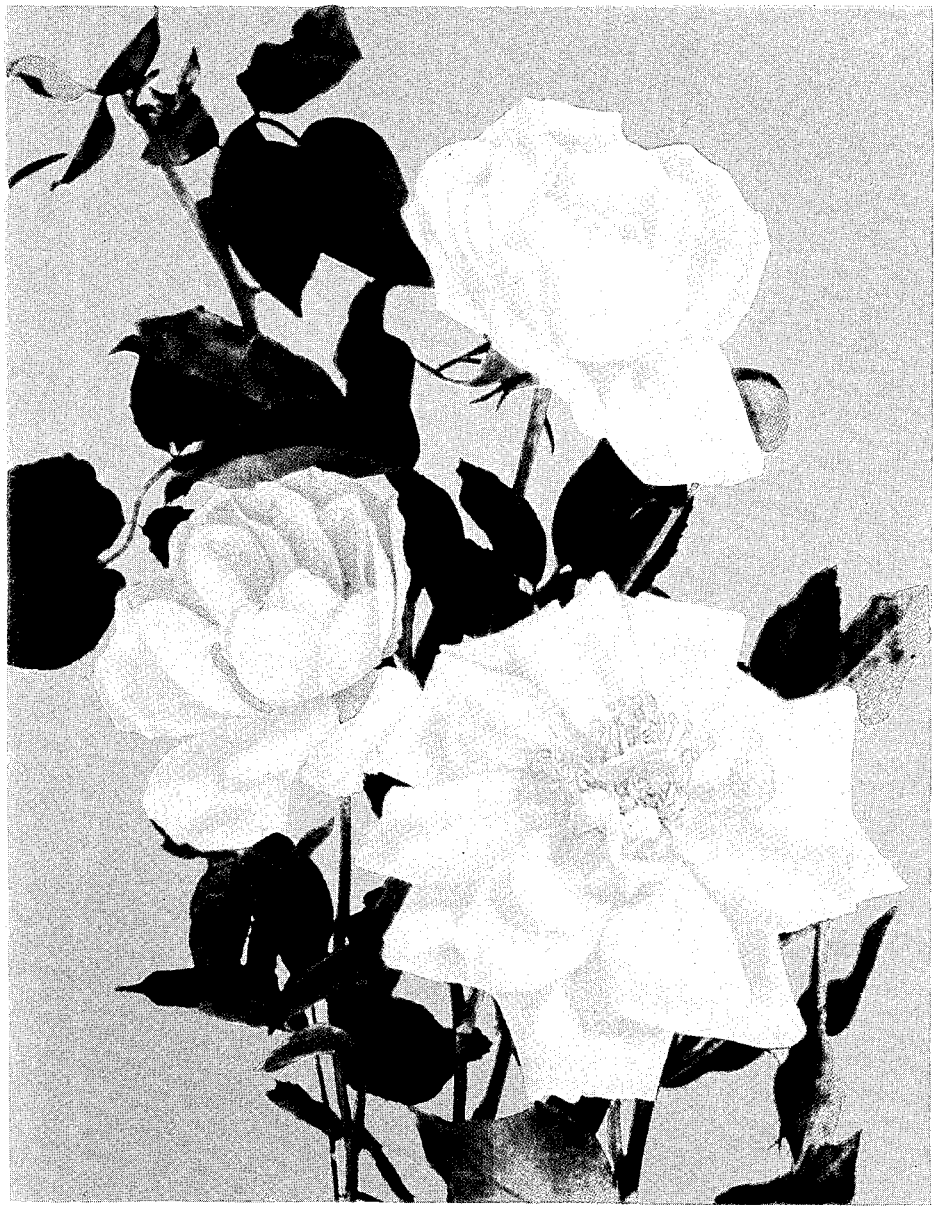
Inventor
W. E. Lammerts
By Robert Robb
His Attorney Patented July 2, 1946

Plant Pat. 704

UNITED STATES PATENT OFFICE

704

ROSE PLANT

Walter E. Lammerts, West Los Angeles, Calif., assignor to Armstrong Nurseries, Inc., Ontario, Calif., a corporation of California Application February 8, 1945, Serial No. 576,741

1 Claim. (Cl. 47—61)

The present invention relates to a new and distinct variety of rose plant in the class of hybrid Pernetiana teas, originated by the crossing of the well-known variety "Sister Therese" and "Captain Thomas," well disclosed in Plant Patent No. 393.

This new rose is characterized as to novelty by the depth and brilliance of color of its flowers, not heretofore found in continuous blooming hybrid tea×hybrid Pernetiana yellow pillar roses; by a high degree of resistance to fading, unlike the normal tendency to fade that is very pronounced in yellow roses, particularly at the tips of the petals, the present variety approximating uniformity in coloring from the base of the petals to the apex; and by a continuity of bloom not heretofore found in double yellow pillar rose types.

Additionally to the above flower characteristics, the foliage of the present variety shows a very high degree of mildew resistance for its class, the foliage developing heavy, glossy and leathery on a free-branching, vigorous plant, relatively free from prickles, all as hereinafter more particularly set forth and illustrated in the accompanying drawing.

Asexual reproduction of this new variety shows the foregoing characteristics come true to form and are established.

The following is a detailed description of this new variety, the color terminology being in accord with the Robert F. Wilson Horticultural Colour Chart, except where otherwise designated as taken from Ridgway's Color Standard:

Type: Tall; pillar; outdoor; seedling; for cut flowers and garden decoration.
Class: Hybrid Pernetiana tea.
Breeding: Seedling.

*Seed parent.*—"Sister Therese" (Soeur Therese).
*Pollen parent.*—"Captain Thomas" (Pl. Pat. #393).

Propagation: Holds its distinguishing characteristics through succeeding propagations by budding, which is the only method tried up to the present.

*Flower*

Locality where grown: Ontario, California.
Flowers borne: Several to stem; in irregular, pyramidal cluster; on normal to strong medium-length stems.
Quantity of bloom: Free; outdoors.
Continuity: Continuous.
Fragrance: Moderate; spicy, slightly fruity.
Bud:

*Pedicel.*—Medium to long; slender; medium stiff; medium rough; numerous gland-tipped cilia and few prickles.

*Color.*—Near Absinthe Green, Plate XXXI (Ridgway). Side exposed to sun tinted with near Verona Brown, Plate XXIX (Ridgway).

*Before calyx breaks.*—*Size*—small to medium. *Form*—long, pointed to ovoid, without a conspicuous neck; with foliaceous appendages, tomentum, gland-tipped cilia, glandular bloom, on the surface of the bud; with slender, much cut foliaceous parts extending beyond the tip of the bud equal to ¼ or more of its length.

*As calyx breaks.*—Near Sulphur Yellow, Plate 1/1. Blotched and pencilled with near Jasper Red, Plate 018. Inner surface—usually two sepals with stipitate glands only and three sepals with stipitate glands and woolly tomentum.

*As first petal opens.*—*Size*—medium. *Form*—long; pointed to urn-shape. *Color*—outside: near Lemon Yellow, Plate 4/1, usually blotched with near Jasper Red, Plate 018; Inside: near Lemon Yellow, Plate 4, tinted toward the apex with near Jasper Red, Plate 018. *Opening*—opens up well; is not prevented from opening by cold, hot, wet or dry weather.

Bloom:

*Size.*—When fully open, small to medium; three inches to four inches.

*Petalage.*—Double, but the stamens not hidden; from 25 to 30 petals arranged irregularly.

*Form.*—Cupped at first; becoming flat; petals remaining at first loosely cupped; becoming later, at maturity, very loosely rolled outward.

Petals: Leathery; with inside satiny and outside shiny.

*Shape.*—Outside—obovate; scalloped with apex flat, with 1 to 2 notches. Intermediate—obovate; scalloped with apex flat, with 1 to 2 notches. Inside—obovate; scalloped irregular with apex flat, with 1 notch.

*Color.*—Colors may be modified by being blotched or tinted with other colors.

This description of a newly opened flower was made from a rose grown outdoors in the month of October, 1944, at Ontario, California:

*Color.*—*Outside petal*—outside surface: near Aureolin, Plate 3/2, usually with small stripe of near Jasper Red, Plate 018/2, from near base toward apex; inside surface: near Aureolin, plate 3/1. *Intermediate petal*—outside surface: near Aureolin, Plate 3/2; inside surface: near Aureolin, Plate 3/1. *Inner petal*—outside surface: near Aureolin, Plate 3/2; inside surface: near Aureolin, Plate 3/1.

This description was made from a rose that was open for three days indoors in the month of October, 1944, at Ontario, California.

*Color.—Outside petal*—outside surface: near Aureolin, Plate 3/1, blotched and striped with near Jasper Red, Plate 018/2; inside surface: near Aureolin, Plate 3/1. *Inside petal*—outside surface: near Aureolin, Plate 3; inside surface: near Aureolin, Plate 3.

*General color effect.*—Newly opened flower—near Aureolin, Plate 3/2. Three days open—near Aureolin, Plate 3/1.

*Behavior.*—Drop off cleanly. Fades only very slightly in hot weather.

*Flower longevity.*—On bush in garden—1 to 3 days in October. Cut roses grown outdoors kept at living room temperatures—2 to 3 days in October.

*Reproductive organs*

Stamens: Many; arranged irregularly about pistils, mixed with petaloids.

Filaments: Long, near Jasper Red, Plate 018, at base, changing to near Lemon Yellow, Plate 4/1, towards anthers. Most with anthers.

Anthers: Medium large; open at various times.

*Color.*—Near Lemon Yellow, Plate 4/1, edges tinted with near Jasper Red, Plate 018/2.

Pollen: Moderate; white.

Pistils: Medium number.

Styles: Uneven; medium length; medium heavy; bunched.

*Color.*—Near Claret Rose, Plate 021.

Stigma: White.

Ovaries: Some enclosed in, some protruding from, calyx.

Hips: Short; flatly globular, with inconspicuous neck; moderately smooth; glandular; walls thick, fleshy.

*Color.*—Near Light Elm Green Plate XVII (Ridgway).

Sepals: Permanent; moderately long; spear-shaped to curled.

*Color—Inside*—near Light Elm Green, Plate XVII (Ridgway) overlaid with white tomentum. Outside—near Biscay Green, Plate XVII (Ridgway).

Seeds: Few; medium large.

Foliage:

*Leaves.*—Compound of 5 to 7 leaflets; normally abundant; medium to large; moderately heavy, leathery, glossy.

*Leaflets.*—Shape—ovoid, with apex acute; base round; irregularly serrate.

*Color.*—Mature—upper surface: near Dark Dull Yellow Green, Plate XXXII (Ridgway); under surface: near Light Elm Green, Plate XVII (Ridgway). *Young*—upper surface: near Cress Green, Plate XXXI (Ridgway); shaded toward margin with near Dark Livid Brown, Plate XXXIX (Ridgway); under surface: near Pois Green, Plate XLI (Ridgway), shaded toward margins with near Deep Livid Brown, Plate XXXIX (Ridgway).

*Rachis.*—Medium to heavy. Upper side—grooved, hairy, glandular; under side—moderately smooth.

*Stipules.*—Moderately long; medium wide; with moderately short points usually, turning out at an angle of more than 45° recurved toward the stem.

*Disease.*—Resistant to mildew.

Growth:

*Habit.*—Upright; pillar; much branched.

*Growth.*—Moderately vigorous.

*Canes.*—Moderately heavy.

*Main stems.*—Near Biscay Green, Plate XVII (Ridgway). *Large prickles*—medium to long; few; very slightly hooked downward; with long, narrow base. *Color*—Near Pecan Brown, Plate XXVIII (Ridgway). *Small prickles*—none. *Hairs*—none.

*Branches.*—Near Biscay Green, Plate XVII (Ridgway). *Large prickles*—few; medium long; slightly hooked downward; with long, narrow base. *Color*—near Deep Purplish Vinaceous, Plate XLIV (Ridgway). *Small prickles*—few. *Hairs*—none.

*New shoots.*—Near Biscay Green, Plate XVII (Ridgway). Side exposed to sun shaded with near Deep Livid Brown, Plate XXXIX (Ridgway). *Large prickles*—few; medium to long; slightly hooked downward; with long, narrow base. *Color*—near deep Livid Brown, Plate XXXIX (Ridgway). *Small prickles*—few. *Hairs*—none.

I claim:

A new and distinct variety of rose plant, characterized as to novelty by the depth, brilliance and uniformity of color of its blooms; resistance of such blooms to fading; unusual continuity of blooming for double yellow pillar type of roses; the heavy, glossy and leathery foliage on a free-branching, vigorous plant relatively free from prickles; and marked resistance of said foliage to mildew, substantially as shown and described.

WALTER E. LAMMERTS.